United States Patent
Hoffman (10) Patent No.: US 6,819,738 B2
(45) Date of Patent: Nov. 16, 2004

(54) HYBRID SCINTILLATOR/PHOTO SENSOR & DIRECT CONVERSION DETECTOR

(75) Inventor: David Michael Hoffman, New Berlin, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 159 days.

(21) Appl. No.: 10/064,775

(22) Filed: Aug. 15, 2002

(65) Prior Publication Data

US 2004/0032927 A1 Feb. 19, 2004

(51) Int. Cl.$^7$ ................................................ A61B 6/00
(52) U.S. Cl. ............................ 378/19; 378/4; 378/9; 250/370.09
(58) Field of Search ........................ 378/4, 9, 15, 19, 378/98.8; 250/370.07, 370.08, 370.09, 370.11, 366

(56) References Cited

U.S. PATENT DOCUMENTS

| | | | |
|---|---|---|---|
| 5,400,387 A | | 3/1995 | Gard et al. .................. 378/207 |
| 6,072,851 A | * | 6/2000 | Sivers .......................... 378/15 |
| 6,324,240 B1 | * | 11/2001 | Yan et al. ....................... 378/4 |
| 6,421,411 B1 | | 7/2002 | Hsieh ............................. 378/4 |
| 6,421,412 B1 | * | 7/2002 | Hsieh et al. .................... 378/9 |
| 2002/0087073 A1 | | 7/2002 | Hoffman ..................... 600/425 |

\* cited by examiner

Primary Examiner—Edward J. Glick
Assistant Examiner—Courtney Thomas
(74) Attorney, Agent, or Firm—Cantor Colburn LLP

(57) ABSTRACT

A hybrid scintillation/direct conversion computed tomography (CT) imaging system including: a gantry, wherein the gantry defines a patient cavity and includes an x-ray source and a radiation detection apparatus, wherein the radiation detection apparatus includes a first radiation detector and a second radiation detector and wherein the x-ray source and the radiation detection apparatus are rotatingly associated with the gantry so as to be separated by the patient cavity; a patient support structure movingly associated with the gantry so as to allow communication with the patient cavity; and a processing device, wherein the processing device is communicated with the radiation detection apparatus. In addition, a method for differentiating material characteristics using a hybrid scintillation/direct conversion imaging system including: obtaining the hybrid scintillation/direct conversion imaging system, wherein the hybrid scintillation/direct conversion imaging system includes a radiation source and a radiation detector apparatus having a first radiation detector and a second radiation detector; operating the imaging system so as to cause the radiation source to emit a radiation beam toward the radiation detector apparatus such that the first radiation detector generates first detector data and the second radiation detector generates second detector data; and processing the first detector data and the second detector data so as to generate image data. In an alternative embodiment, a medium encoded with a machine-readable computer program code for differentiating material characteristics using a hybrid scintillation/direct conversion imaging system, the medium including instructions for causing a controller to implement the aforementioned method.

45 Claims, 5 Drawing Sheets

HYBRID SCINTILLATOR/PHOTO SENSOR & DIRECT CONVERSION DETECTOR

BACKGROUND OF INVENTION

This invention relates generally to a system and method for differentiating material characteristics using an imaging system and more particularly to a system and method for differentiating material characteristics using a hybrid scintillator/photo sensor and direct conversion (DC) imaging system.

In at least one known computed tomography (CT) imaging system configuration having single and/or multi-slice scintillator/photo diode arrays, an x-ray source projects a fan-shaped, or a cone-shaped, beam which is collimated to lie within an X-Y-Z volume of a Cartesian coordinate system, wherein the X-Y-Z volume is generally referred to as an "imaging volume" and usually includes a set of X-Y planes generally referred to as the "imaging planes". An array of radiation detectors, wherein each radiation detector includes a detector element, is disposed within the CT system so as to receive this beam. An object, such as a patient, is disposed within the imaging plane so as to be subjected to the x-ray beam wherein the x-ray beam passes through the object. As the x-ray beam passes through the object being imaged, the x-ray beam becomes attenuated before impinging upon the array of radiation detectors. The intensity of the attenuated beam radiation received at the detector array is responsive to the attenuation of the x-ray beam by the object, wherein each detector element produces a separate electrical signal responsive to the beam attenuation at the detector element location. These electrical signals are referred to as x-ray attenuation measurements.

In addition, the x-ray source and the detector array may be rotated, with a gantry within the imaging volume, around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles during one revolution of the x-ray source and the detector array. In an axial scan, the projection data is processed so as to construct an image that corresponds to two-dimensional slices taken through the object.

One method for reconstructing an image from a set of projection data is referred to as the "filtered back-projection technique". This process converts the attenuation measurements from a scan into discrete integers, ranging from –1024 to +3072, called "CT numbers" or "Hounsfield Units" (HU). These HU's are used to control the brightness of a corresponding pixel on a cathode ray tube or a computer screen display in a manner responsive to the attenuation measurements. For example, an attenuation measurement for air may convert into an integer value of –1000HU's (corresponding to a dark pixel) and an attenuation measurement for very dense bone matter may convert into an integer value of +3000 (corresponding to a bright pixel), whereas an attenuation measurement for water may convert into an integer value of 0HU's (corresponding to a gray pixel). This integer conversion, or "scoring" allows a physician or a technician to determine the density of matter based on the intensity of the computer display and thus locate and identify areas of concern.

Typically, radiation detector arrays used in imaging systems, such as the CT imaging system described hereinabove, include single and/or multi-slice scintillator/photo diode detectors. A scintillation detector is constructed of a scintillation material, such as cadmium tungstate (CdWO4) or rare earth ceramics and operates by receiving x-ray photons emitted by an x-ray source and converting these x-ray photons into a digital signal proportional to the attenuated x-ray energy received. These digital signals are then processed and turned into image data.

One goal of CT imaging has been to utilize multi-energy scanning techniques to differentiate between tissues and/or materials having varying atomic numbers and densities, such as calcium and/or iodine. Historically, this has been accomplished using an imaging system having a scintillation detector either by taking single slice images with a single slice CT imaging system having two different x-ray beam filters, or by taking single slice images with a single slice CT imaging system having two different x-ray tube kVp's that exactly overlap spatially, but at a slightly later time, and then processing these two images to separate materials having varying atomic numbers and densities, using suitable known methods such as image subtraction. For example, using a single slice CT imaging system a first single slice image would be obtained. The x-ray kVp or the filter at the x-ray tube would then be changed and a second single slice image would be obtained at the same patient location. As mentioned above, the two slices of image data would then be processed to separate materials of varying atomic numbers and densities within the obtained slice plane.

Unfortunately, this is an expensive, time consuming and involved process and although a CT imaging system having a DC detector could be conceivably utilized exclusively as the CT imaging system for performing the above mentioned process, the DC detector would not be able to count the x-rays fast enough to support CT flux rates and/or scan times. Thus, if used in the current mode the obtained information would suffer from very high amount of non-linearities that would be very difficult or even impossible to correct in order to achieve artifact free scanning.

The above discussed and other features and advantages of the embodiments will be appreciated and understood by those skilled in the art from the following detailed description and drawings

SUMMARY OF INVENTION

The above discussed and other drawbacks and deficiencies are overcome or alleviated by a hybrid scintillation/direct conversion computed tomography (CT) imaging system comprising: a gantry, wherein the gantry defines a patient cavity and includes an x-ray source and a radiation detection apparatus, wherein the radiation detection apparatus includes a first radiation detector and a second radiation detector and wherein the x-ray source and the radiation detection apparatus are rotatingly associated with the gantry so as to be separated by the patient cavity; a patient support structure movingly associated with the gantry so as to allow communication with the patient cavity; and a processing device, wherein the processing device is communicated with the radiation detection apparatus.

In an alternative embodiment, a method for differentiating material characteristics using a hybrid scintillation/direct conversion imaging system comprising: obtaining the hybrid scintillation/direct conversion imaging system, wherein the hybrid scintillation/direct conversion imaging system includes a radiation source and a radiation detector apparatus having a first radiation detector and a second radiation detector; operating the imaging system so as to cause the radiation source to emit a radiation beam toward the radiation detector apparatus such that the first radiation detector generates first detector data and the second radiation detector generates second detector data; and processing the first detector data and the second detector data so as to generate image data.

In another alternative embodiment, a hybrid scintillation/direct conversion imaging system, comprising: a gantry, wherein the gantry defines a patient cavity and includes a radiation source and a radiation detection apparatus, wherein the radiation detection apparatus includes a first radiation detector and a second radiation detector and wherein the radiation source and the radiation detection apparatus are rotatingly associated with the gantry so as to be separated by the patient cavity; a patient support structure movingly associated with the gantry so as to allow communication with the patient cavity; and a processing device, for obtaining data from the first radiation detector and the second radiation detector.

In another alternative embodiment, a medium encoded with a machine-readable computer program code for differentiating material characteristics using a hybrid scintillation/direct conversion imaging system, wherein the hybrid scintillation/direct conversion imaging system includes a radiation source and a radiation detector apparatus having a first radiation detector and a second radiation detector, the medium including instructions for causing controller to implement a method comprising: operating the imaging system so as to cause the radiation source to emit a radiation beam toward the radiation detector apparatus such that the first radiation detector generates first detector data and the second radiation detector generates second detector data; and processing the first detector data and the second detector data so as to generate image data.

In another alternative embodiment, a computer data signal, comprising: code configured to cause a processor to implement a method for differentiating material characteristics using a hybrid scintillation/direct conversion imaging system, wherein the hybrid scintillation/direct conversion imaging system includes a radiation source and a radiation detector apparatus having a first radiation detector and a second radiation detector, the method further comprising: operating the imaging system so as to cause the radiation source to emit a radiation beam toward the radiation detector apparatus such that the first radiation detector generates first detector data and the second radiation detector generates second detector data; and processing the first detector data and the second detector data so as to generate image data.

BRIEF DESCRIPTION OF DRAWINGS

Referring to the exemplary drawings wherein like elements are numbered alike in the several Figures.

DETAILED DESCRIPTION

Figure 1:
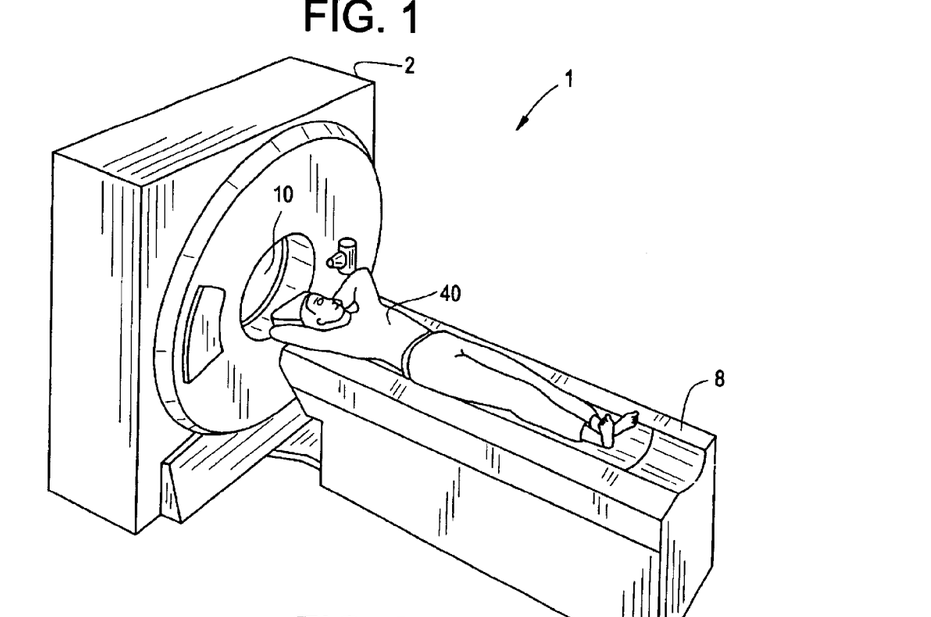
FIG. 1 is a perspective view of a CT imaging system and a patient disposed for imaging.
Figure 2A:
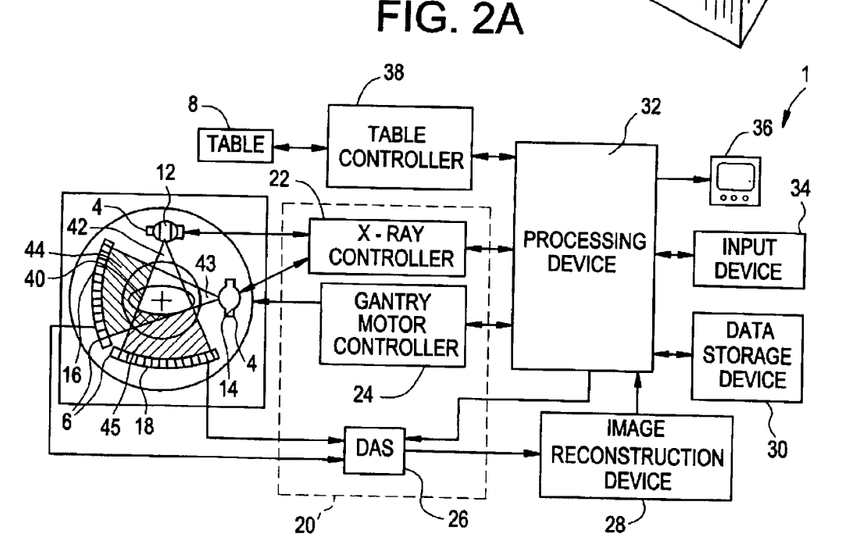
FIG. 2A is a block schematic diagram of a hybrid scintillation/direct conversion CT imaging system in accordance with a first embodiment.
Figure 2B:
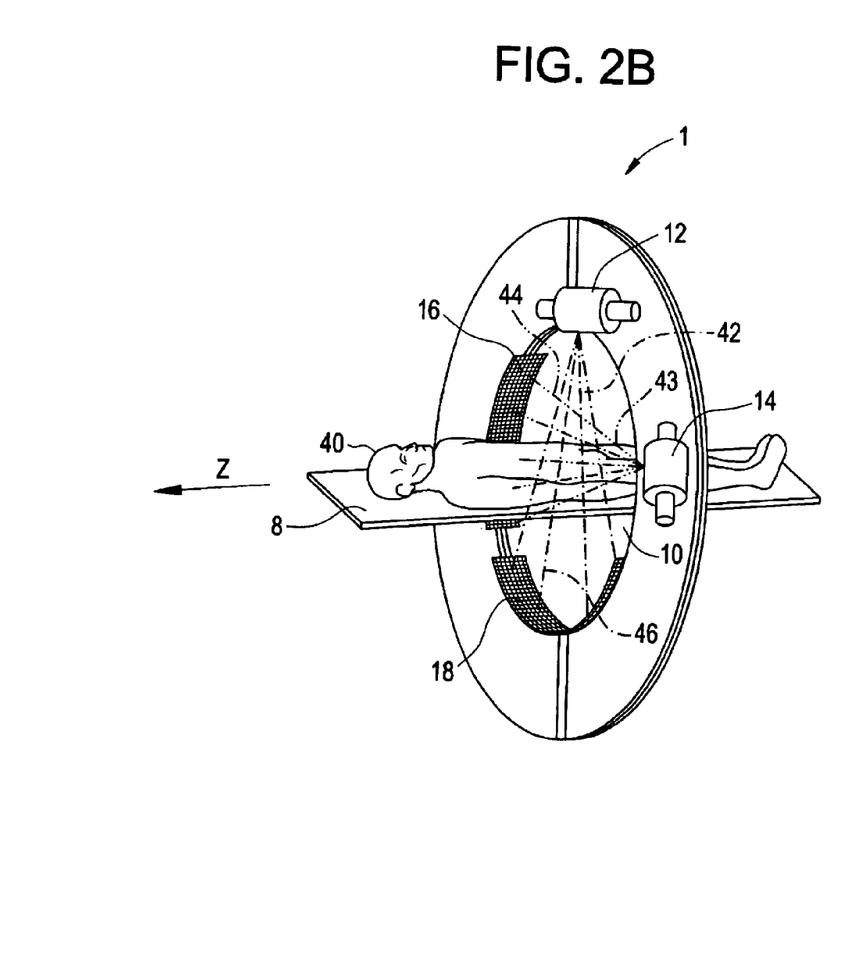
FIG. 2B is a sectional perspective view of a gantry for a hybrid scintillation/direct conversion CT imaging system in accordance with a first embodiment.

Referring to FIG. 1, FIG. 2A and FIG. 2B, a first embodiment of a hybrid scintillation/direct conversion CT imaging system 1 is shown and discussed. Hybrid scintillation/direct conversion CT imaging system 1 includes a gantry 2 having an x-ray source 4, a radiation detection apparatus 6, a patient support structure 8 and a patient cavity 10, wherein x-ray source 4 and radiation detection apparatus 6 are disposed so as to be separated by patient cavity 10. X-ray source 4 and radiation detection apparatus 6 are rotatingly disposed relative to gantry 2 and patient support structure 8, so as to allow x-ray source 4 and radiation detection apparatus 6 to rotate around patient support structure 8 when patient support structure 8 is disposed within patient cavity 10. X-ray projection data is obtained by rotating x-ray source 4 and radiation detection apparatus 6 around patient cavity 10 during a scan.

X-ray source 4 includes a first x-ray emitter 12 and a second x-ray emitter 14 radiation detection apparatus 6 includes a first radiation detector 16 and a second radiation detector 18. First x-ray emitter 12 is opposingly disposed relative to first radiation detector 16 such that first x-ray emitter 12 and first radiation detector 16 are separated by patient cavity 10. Moreover, second x-ray emitter 14 is opposingly disposed relative to second radiation detector 18 such that second x-ray emitter 14 and second radiation detector 18 are separated by patient cavity 10.

X-ray source 4 and radiation detection apparatus 6 are communicated with a control mechanism 20 associated with CT imaging system 1. Control mechanism 20 controls the rotation and operation of x-ray source 4 and/or radiation detection apparatus 6. Control mechanism 20 includes an x-ray controller 22 communicated with x-ray source 4, a gantry motor controller 24, and a data acquisition system (DAS) 26 communicated with radiation detection apparatus 6, wherein x-ray controller 22 provides power and timing signals to x-ray source 4, gantry motor controller 24 controls the rotational speed and angular position of x-ray source 4 and radiation detection apparatus 6 and DAS 26 receives the electrical signal data produced by radiation detection apparatus 6 and converts this data into digital signals for subsequent processing. CT imaging system 1 also includes an image reconstruction device 28, a data storage device 30 and a processing device 32, wherein processing device 32 is communicated with image reconstruction device 28, gantry motor controller 24, x-ray controller 22, data storage device 30, an input device 34 and an output device 36. Moreover, CT imaging system 1 also includes a table controller 38 communicated with processing device 32 and patient support structure 8, so as to control the position of patient support structure 8 relative to patient cavity 10.

Figure 3:
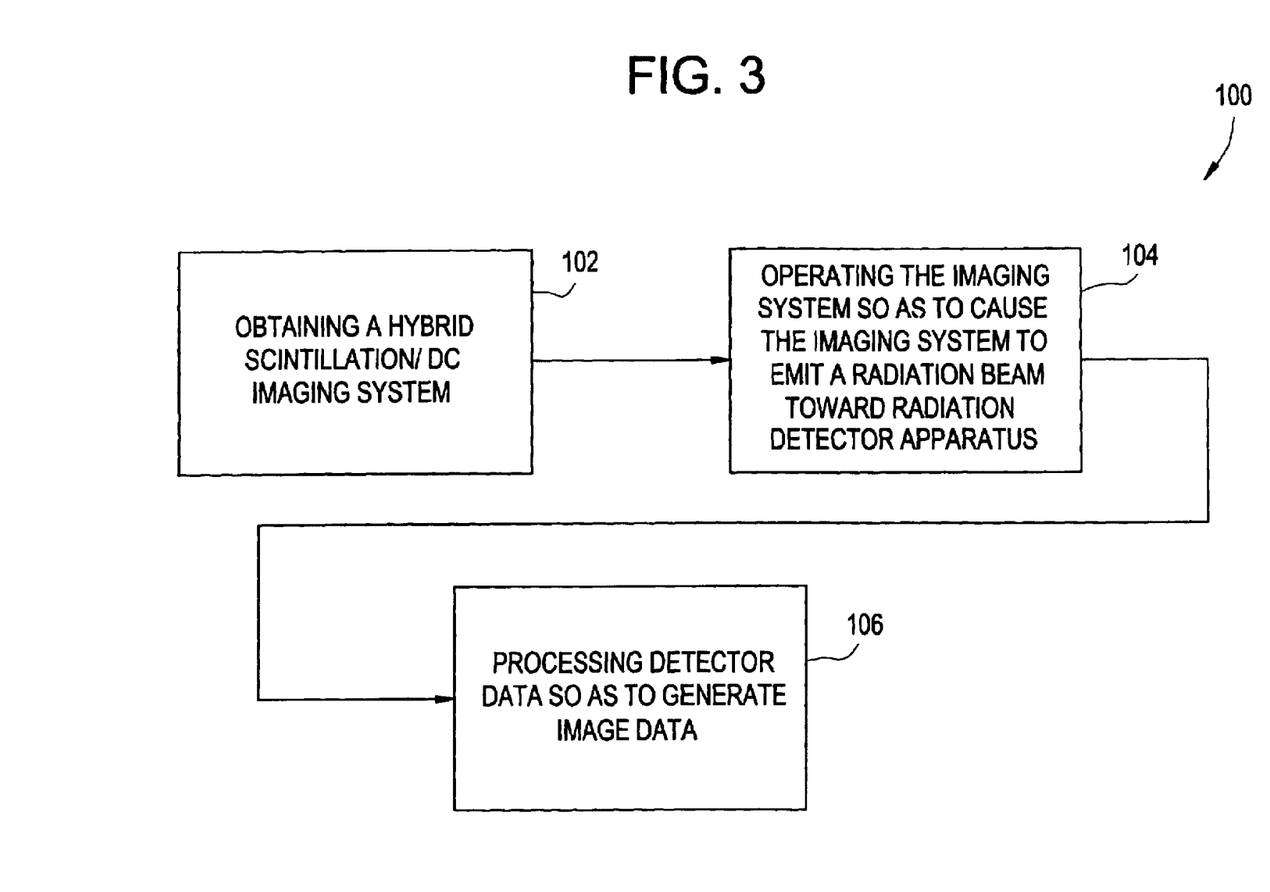
FIG. 3 is a block diagram describing a method for differentiating material characteristics using a hybrid scintillation/direct conversion CT imaging system.

Referring to FIG. 3, a method 100 for differentiating material characteristics, such as material types and densities, using a hybrid scintillation/direct conversion imaging system 1 in accordance with a first embodiment is shown and discussed. Hybrid scintillation/direct conversion imaging system 1 is obtained as shown in block 102 wherein imaging system 1 includes a x-ray source 4 having a first x-ray emitter 12 and a second x-ray emitter 14 and a radiation detector apparatus 6 having a first radiation detector 16 and a second radiation detector 18. A patient 40 is disposed upon patient support structure 8 and patient support structure 8 is disposed within patient cavity 10. Imaging system 1 is then operated as shown in block 104 so as to cause first x-ray emitter 12 to emit and project a first x-ray beam 42 toward first radiation detector 16 and so as to cause second x-ray emitter 14 to emit and project second x-ray beam 43 toward second radiation detector 18. As first x-ray beam 42 and second x-ray beam 43 pass through patient 40, a first attenuated x-ray beam 44 and a second attenuated x-ray beam 45 are created, wherein first attenuated x-ray beam 44 and second attenuated x-ray beam 45 are responsive to patient 40. First x-ray beam 42 and second x-ray beam 43 may be collimated by a collimate so as to lie within an X-Y-Z volume of a Cartesian coordinate system referred to as an "imaging volume". After passing through and becoming attenuated by patient 40, first radiation detector 16 receives first attenuated x-ray beam 44 and second radiation detector 18 receives second attenuated x-ray beam 45, thus causing first radiation detector 16 to generate first detector data and second radiation detector 18 to generate second detector data, wherein first detector data and second detector data are generated in a manner responsive to first attenuated x-ray beam 44 and second attenuated x-ray beam 45, respectively.

First detector data and second detector data are then processed so as to generate image data as shown in block 106. This is accomplished by communicating first detector data and second detector data to DAS 26, which then converts first detector data and second detector data into digital signals responsive to patient 40. First detector data, second detector data and the digital signals are then communicated to image reconstruction device 28, which generates image data by performing high-speed image reconstruction. This information is then communicated to processing device 32, which stores the image data in data storage device 30 and displays the image data as an image via output device 36.

When hybrid scintillation/direct conversion imaging system 1 is used in a "step and shoot" or single non-helical mode, various slice planes through patient 40 may be viewed by multiple detector cells in the Z direction. If two different types of tubes/detectors were disposed at various angular positions around patient 40, a plurality of different image data having different informational content may be obtained simultaneously. When hybrid scintillation/direct conversion imaging system 1 is used in a helical mode, adjacent slice planes through patient 40 may be viewed by multiple detector cells in the Z direction at slightly later points in time, it the rotational pitch of the radiation detection apparatus 6 had the appropriate width. Similarly, if two different types of radiation detectors were placed adjacent to each other in the Z direction, then adjacent slice planes through patient 40 could be viewed by multiple radiation detectors of a different type in the Z direction at slightly later points in time, again allowing for an appropriate rotational pitch of radiation detection apparatus 6. Similarly, if two different types of radiation detectors were placed at various angular positions, but displace relative to each other in the Z direction, then adjacent slice planes through patient 40 could be viewed by multiple radiation detectors of a different type in the Z direction at slightly later points in time, again allowing for an appropriate rotational pitch of radiation detection apparatus 6.

In accordance with a first embodiment, first radiation detector 16 may be a scintillator detector/photo-sensor detector so as to allow for the collection of traditional information for creating anatomical detail for CT slices and second radiation detector 18 may be a direct conversion (DC) detector configured in an x-ray counting and energy discrimination mode so as to count the attenuated x-rays and so as to measure the attenuated x-ray energy. This information on the number and energy of the attenuated x-rays may provide tissue differentiation data that provides information about the elemental composition and/or density of various tissue materials, so as to allow for the discrimination of iodine, calcium and/or other materials as well. The information obtained from first radiation detector 16 and second radiation detector 18 may be super positioned to create a single image having identically positioned and overlapping information of anatomical detail and/or tissue discrimination (material type and density). Second radiation detector 18 may be of a single slice design and/or a multiple slice design. The multiple slice design may provide information on a variety of different tissue materials, whereas the multiple slice design may be integrated across multiple slices for improved statistics on an individual basis.

When second radiation detector 18 is used in the x-ray counting and energy discrimination mode, very little x-ray dose is added to the CT exam because of the low level of x-rays required for energy discrimination. This implementation may be accomplished quickly because DC detectors currently operate in the x-ray counting and energy discrimination mode in existing BMD and GAMMA camera systems. This embodiment may allow for obtaining super position of anatomical detail and tissue characterization information and/or the measurement and correction of scatter. The DC detector may be used to pre-measure patient 40 and adjust the CT system mA within a slice and/or from slice to slice in the area of the scintillator detector. Furthermore, the energy discrimination (ED) information obtained may be used to implement smart CT correction schemes, such as beam hardening and/or smart detector correction schemes. Also, in accordance with a first embodiment multiple types of operational modes may be implemented. The x-ray beam average kV may be varied in the Z direction if an x-ray attenuation material was provided at the x-ray tube and/or at the radiation detection apparatus 6 so as to enhance the collection of multi-energy x-ray information in the area of the DC detector. The information obtained via the DC detector may then be processed so as to separate different densities of materials within a patient slice plane in a simple operational mode. Additionally, multiple multi-energy CT slices taken at the same time as standard CT slices may be obtained for a different anatomical area and later super positioned so as to separate multiple types of materials.

This embodiment allows the first x-ray beam 42, the second x-ray beam 43 and the beam filtration to be tailored for a desired system performance and also allows for the use of beams having different energies. It should be noted that each row detector can differentiate between multiple types of materials. As such, with multiple slices information can be obtained for a larger amount of different materials. The different operational modes allow for the detection of different materials using each detector row. They also allow multiple detector rows to be integrated for statistical quantification, analysis and correction, such as for improving signal to noise ratio.

Figure 4A:
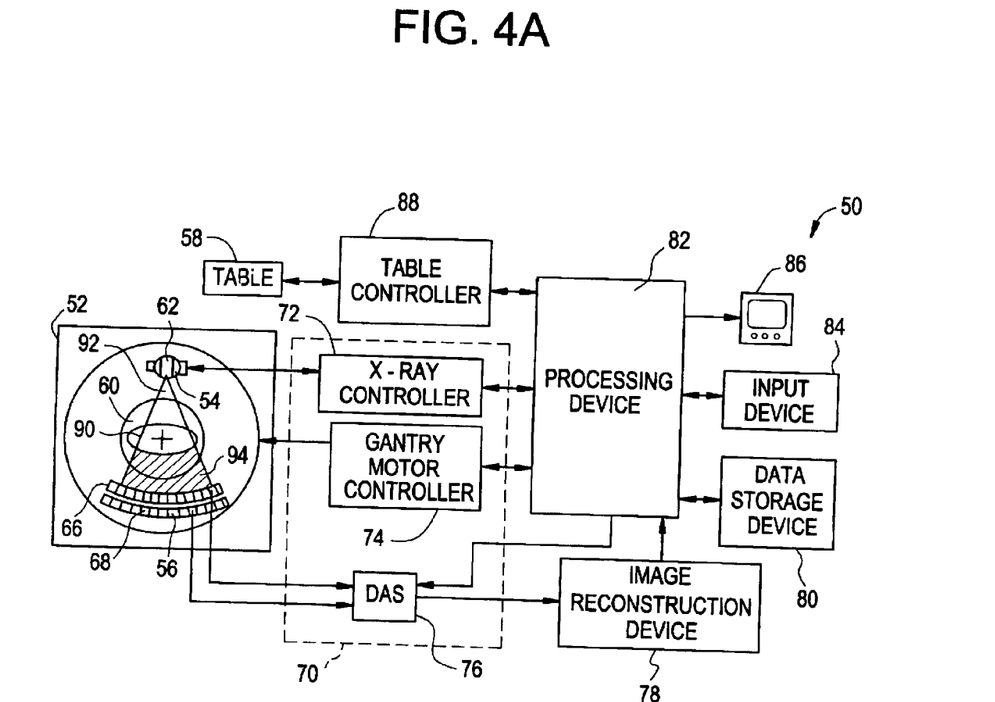
FIG. 4A is a block schematic diagram of a hybrid scintillation/direct conversion CT imaging system in accordance with a second embodiment.
Figure 4B:
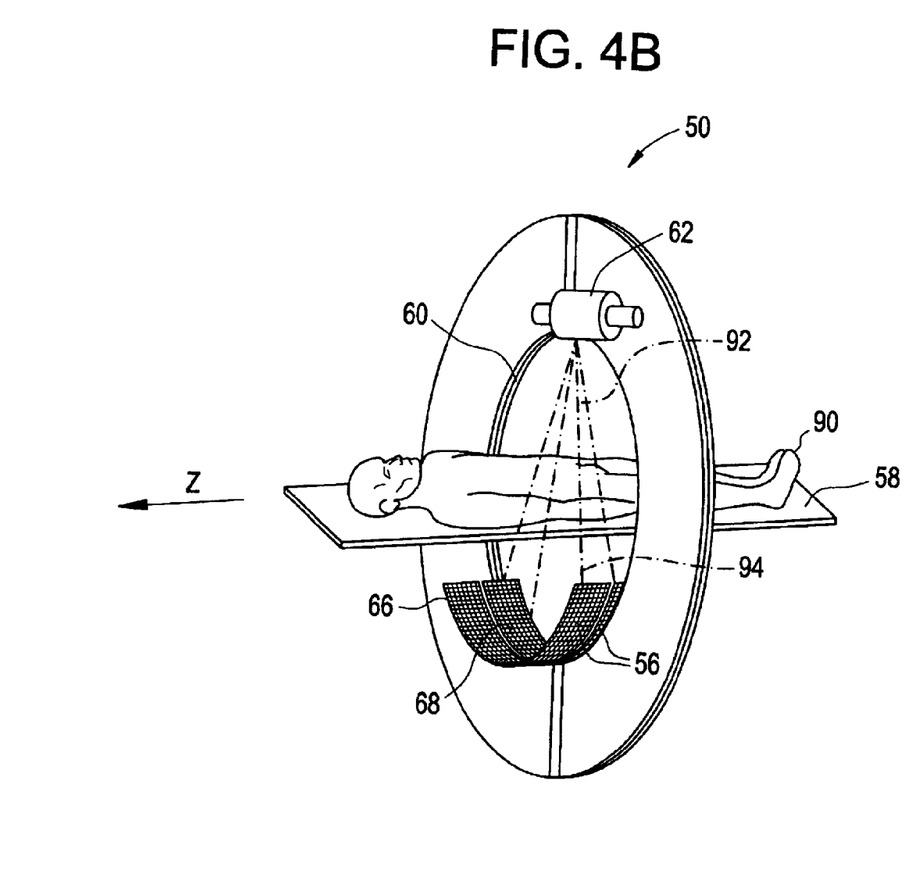
FIG. 4B is a sectional perspective view of a gantry for a hybrid scintillation/direct conversion CT imaging system in accordance with a second embodiment.

Referring to FIG. 1, FIG. 4A and FIG. 4B, a second embodiment of a hybrid scintillation/direct conversion CT imaging system 50 is shown and discussed. Hybrid scintillation/direct conversion CT imaging system 50 includes a gantry 52 having an x-ray source 54, a radiation detection apparatus 56, a patient support structure 58 and a patient cavity 60, wherein x-ray source 54 and radiation detection apparatus 56 are disposed so as to be separated by patient cavity 60. X-ray source 54 and radiation detection apparatus 56 are rotatingly disposed relative to gantry 52 and patient support structure 58, so as to allow x-ray source 54 and radiation detection apparatus 56 to rotate around patient support structure 58 when patient support structure 58 is disposed within patient cavity 60. X-ray projection data is obtained by rotating x-ray source 54 and radiation detection apparatus 56 around patient 60 during a scan.

X-ray source 54 includes a first x-ray emitter 62 and radiation detection apparatus 56 includes a first radiation detector 66 and a second radiation detector 68. First x-ray emitter 62 is opposingly disposed relative to first radiation detector 66 and second radiation detector 68 such that first x-ray emitter 62 is separated from first radiation detector 66 and second radiation detector 68 by patient cavity 60. X-ray source 54 and radiation detection apparatus 56 are communicated with a control mechanism 70 associated with CT imaging system 50. Control mechanism 70 controls the rotation and operation of x-ray source 54 and/or radiation detection apparatus 56. Control mechanism 70 includes an x ray controller 72 communicated with x-ray source 54, a gantry motor controller 74, and a data acquisition system (DAS) 76 communicated with radiation detection apparatus 56, wherein x-ray controller 72 provides power and timing signals to x-ray source 54, gantry motor controller 74 controls the rotational speed and angular position of x-ray source 54 and radiation detection apparatus 56 and DAS 76 receives the electrical signal data produced by radiation detection apparatus 56 and converts this data into digital signals for subsequent processing. CT imaging system 50 also includes an image reconstruction device 78, a data storage device 80 and a processing device 82, wherein processing device 82 is communicated with image reconstruction device 78, gantry motor controller 74, x-ray controller 72, data storage device 80, an input device 84 and an output device 86. Moreover, CT imaging system 50 also includes a table controller 88 communicated with processing device 82 and patient support structure 58, so as to control the position of patient support structure 58 relative to patient cavity 60.

Referring to FIG. 3, a method 100 for differentiating material characteristics, such as material types and densities, using a hybrid scintillation/direct conversion imaging system 50 in accordance with a second embodiment is shown and discussed. Hybrid scintillation/direct conversion imaging system 50 is obtained as shown in block 102 wherein imaging system 50 includes a radiation source 54 having a first x-ray emitter 62 and a radiation detector apparatus 56 having a first radiation detector 66 and a second radiation detector 68. First radiation detector 66 is disposed so as to be adjacent to second radiation detector 68. A patient 90 is disposed upon patient support structure 58 and patient support structure 58 is disposed within patient cavity 60. Imaging system 50 is then operated as shown in block 104 so as to cause radiation source 54 to emit and project an x-ray beam 92 toward radiation detection apparatus 56 so as to pass through patient 90 and create an attenuated x-ray beam 94, wherein attenuated x-ray beam 94 is responsive to patient 90. X-ray beam 92 may be collimated by a collimate so as to lie within an X-Y-Z volume of a Cartesian coordinate system referred to as an "imaging volume".

After passing through and becoming attenuated by patient 90, radiation detection apparatus 56 receives attenuated x-ray beam 94, thus causing first radiation detector 66 to generate first detector data and second radiation detector 68 to generate second detector data, wherein first detector data and second detector data are generated in a manner responsive to attenuated x-ray beam 94. First detector data and second detector data are then processed so as to generate image data as shown in block 106. This is accomplished by communicating first detector data and second detector data to DAS 76, which then converts first detector data and second detector data into digital signals responsive to patient 90. First detector data, second detector data and the digital signals are then communicated to image reconstruction device 78, which generates image data by performing high-speed image reconstruction. This information is then communicated to processing device 82, which stores the image data in data storage device 80 and displays the image data as an image via output device 86.

When hybrid scintillation/direct conversion imaging system 50 is used in a helical mode, adjacent slice planes through patient 90 may be viewed by multiple detector cells in the Z direction at slightly later points in time, it the rotational pitch of the radiation detection apparatus 56 had the appropriate width. Similarly, if two different types of radiation detectors were placed adjacent to each other in the Z direction, then adjacent slice planes through patient 90 could be viewed by multiple radiation detectors of a different type in the Z direction at slightly later points in time, again allowing for an appropriate rotational pitch of radiation detection apparatus 56.

In accordance with a second embodiment, first radiation detector 66 may be a scintillator detector/photo-sensor detector so as to allow for the collection of traditional information for creating anatomical detail for CT slices and second radiation detector 68 may be a direct conversion (DC) detector configured in an x-ray counting and energy discrimination mode so as to count the attenuated x-rays and so as to measure the attenuated x-ray energy. This information on the number and energy of the attenuated x-rays may provide tissue differentiation data that provides information about the elemental composition and/or density of various tissue materials, so as to allow for the discrimination of iodine, calcium and/or other materials as well. The information obtained from first radiation detector 66 and second radiation detector 68 may be super positioned to create a single image having identically positioned and overlapping information of anatomical detail and/or tissue discrimination (material type and density). Second radiation detector 68 may be of a single slice design and/or a multiple slice design. The multiple slice design may provide information on a variety of different tissue materials, whereas the single slice design may be integrated across multiple slices for improved statistics on an individual basis.

When second radiation detector 68 is used in the x-ray counting and energy discrimination mode, very little x-ray dose is added to the CT exam because of the low level of x-rays required for energy discrimination. This implementation may be accomplished quickly because DC detectors currently operate in the x-ray counting and energy discrimination mode in existing BMD and GAMMA camera systems. This embodiment may allow for obtaining super position of anatomical detail and tissue characterization information, as well as the measurement and correction of scatter. The DC detector may be used to pre-measure patient 90 and adjust the CT system mA within a slice and/or from slice to slice in the area of the scintillator detector. Furthermore, the ED information obtained may be used to implement smart CT correction schemes, such as beam hardening and/or smart detector correction schemes. Also, in accordance with a second embodiment multiple types of operational modes may be implemented. The x-ray beam kVp may be varied in the Z direction if an x-ray attenuation material was provided at the x-ray tube and/or at the radiation detection apparatus 56 so as to enhance the collection of multi-energy x-ray information in the area of the DC detector. The information obtained via the DC detector may then be processed so as to separate different densities of materials within a patient slice plane in a simple operational mode. Additionally, multiple multi-energy CT slices taken at the same time as standard CT slices may be obtained for a different anatomical area and later super positioned so as to separate multiple types of materials.

This embodiment allows the first x-ray beam 92 and the beam filtration to be tailored for a desired system performance and also allows for the use of beams having different energies. It should be noted that each row detector can differentiate between multiple types of materials. As such, with multiple slices information can be obtained for a larger amount of different materials. The different operational modes allow for the detection of different materials using each detector row. They also allow multiple detector rows to be integrated for statistical quantification, analysis and correction, such as for improving signal to noise ratio.

Although first radiation detector 66 is preferably a scintillator type radiation detector, first radiation detector 66 may be any type of radiation detector suitable to the desired end purpose, such as a direct conversion (DC) type radiation detector. In addition, although second radiation detector 68 is preferably a direct conversion (DC) type radiation detector, second radiation detector 68 may be any type of radiation detector suitable to the desired end purpose, such as a scintillator type radiation detector. Although the embodiments described herein are described as applying to a computed tomography imaging system 50, it should be stated that the embodiments described herein may be applied to any imaging system suitable to the desired end purpose, such as PET, MRI, ultrasound and/or an imaging system having a stationary ring and/or arc of detector arrays which surround the patient cavity, wherein the radiation source moves around patient 90 irradiating the detector elements within the stationary ring and/or arc.

In accordance with an exemplary embodiment, a method 100 for differentiating material characteristics using a hybrid scintillation/direct conversion imaging system may be applied by any imaging system suitable to the desired end purpose, such as a magnetic resonance imaging (MRI), ultrasound, X-Ray, CT and/or PET.

In accordance with an exemplary embodiment, processing of FIG. 3 may be implemented through processing device 32, 82 operating in response to a computer program. In order to perform the prescribed functions and desired processing, as well as the computations therefore (e.g., the execution of Fourier analysis algorithm(s), the control processes prescribed herein, and the like), the controller may include, but not be limited to, a processor(s), computer(s), memory, storage, register(s), timing, interrupt(s), communication interfaces, and input/output signal interfaces, as well as combinations comprising at least one of the foregoing. For example, the controller may include input signal filtering to enable accurate sampling and conversion or acquisitions of such signals from communications interfaces. It is also considered within the scope of the invention that the processing of FIG. 3 may be implemented by a controller located remotely from processing device 32, 82.

As described above, the embodiments may be embodied in the form of computer-implemented processes and apparatuses for practicing those processes. The present invention can also be embodied in the form of computer program code containing instructions embodied in tangible media, such as floppy diskettes, CD-ROMs, hard drives, or any other computer-readable storage medium, wherein, when the computer program code is loaded into and executed by a computer, the computer becomes an apparatus for practicing the invention. Existing systems having reprogrammable storage (e.g., flash memory) can be updated to implement the invention. The present invention can also be embodied in the form of computer program code, for example, whether stored in a storage medium, loaded into and/or executed by a computer, or transmitted over some transmission medium, such as over electrical wiring or cabling, through fiber optics, or via electromagnetic radiation, wherein, when the computer program code is loaded into and executed by a computer, the computer becomes an apparatus for practicing the invention. When implemented on a general-purpose microprocessor, the computer program code segments configure the microprocessor to create specific logic circuits.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the scope thereof. Therefore, it is intended that the invention not be limited to the particular embodiment disclosed as the best mode contemplated for carrying out this invention, but that the invention will include all embodiments falling within the scope of the appended claims. Moreover, the use of the terms first, second, etc. do not denote any order or importance, but rather the terms first, second, etc. are used to distinguish one element from another.

What is claimed is:

1. A hybrid scintillation/direct conversion computed tomography (CT) imaging system comprising:

a gantry, wherein said gantry defines a patient cavity and includes an x-ray source and a radiation detection apparatus, wherein said radiation detection apparatus includes a first radiation detector and a second radiation detector and wherein said x-ray source and said radiation detection apparatus are rotatingly associated with said gantry in an X-Y plane so as to be separated by said patient cavity, wherein said first radiation detector is a different type of detector than said second radiation detector, said second radiation detector configured to count attenuated x-rays and measure the energy of said attenuated x-rays;

a patient support structure movingly associated with said gantry in a Z axis substantially transverse to said X-Y plane so as to allow communication with said patient cavity; and a processing device, wherein said processing device is communicated with said radiation detection apparatus.

2. The imaging system of claim 1, wherein said first radiation detector is a scintillator/photo-sensor detector and wherein said second radiation detector is a direct conversion detector.

3. The imaging system of claim 1, wherein said first radiation detector is disposed so as to be adjacent to said second radiation detector relative to said Z axis.

4. The imaging system of claim 1, wherein said first radiation detector is disposed so as to be non-adjacent to said second radiation detector relative to said Z axis and adjacent thereto with respect to said X-Y plane.

5. The imaging system of claim 1, wherein said x-ray source includes a first x-ray emitter opposingly disposed relative to said first radiation detector and wherein said x-ray source includes a second x-ray emitter opposingly disposed relative to said second radiation detector.

6. The imaging system of claim 1, wherein said x-ray source includes a first x-ray emitter opposingly disposed relative to said first radiation detector and said second radiation detector.

7. A method of imaging using a hybrid scintillation/direct conversion imaging system for differentiating material characteristics, the method comprising:

obtaining the hybrid scintillation/direct conversion imaging system, wherein the hybrid scintillation/direct conversion imaging system includes a radiation source and a radiation detector apparatus having a first radiation detector and a second radiation detector, wherein said first radiation detector is a scintillator/photo-sensor detector and wherein said second radiation detector is a direct conversion detector;

operating the imaging system so as to cause said radiation source to emit a radiation beam toward said radiation detector apparatus such that said first radiation detector generates first detector data and said second radiation detector generates second detector data; and processing said first detector data and said second detector data so as to generate image data.

8. The method of claim 7, wherein said obtaining includes obtaining an imaging system defining a patient cavity and having a first x-ray emitter opposingly disposed relative to said first radiation detector and said second radiation detector such that said first x-ray emitter is separated from said first radiation detector and said second radiation detector via said patient cavity.

9. The method of claim 8, wherein said operating includes operating said imaging system so as to cause said first x-ray emitter to project a first x-ray beam toward said first radiation detector;

wherein said first x-ray beam passes through a patient so as to generate a first attenuated x-ray beam, wherein said first attenuated x-ray beam is communicated with said first radiation detector and said second radiation detector.

10. The method of claim 7, wherein said obtaining includes obtaining an imaging system having a first x-ray emitter, a second x-ray emitter and defining a patient cavity;

wherein said first x-ray emitter is opposingly disposed relative to said first radiation detector so as to be separated by said patient cavity; and wherein said second x-ray emitter is opposingly disposed relative to said second radiation detector so as to be separate by said patient cavity.

11. The method of claim 10, wherein said operating includes operating said imaging system so as to cause said first x-ray emitter to project a first x-ray beam toward said first radiation detector and so as to cause said second x-ray emitter to project a second x-ray beam toward said second radiation detector;

wherein said first x-ray beam passes through a patient so as to generate a first attenuated x-ray beam, wherein said first attenuated x-ray beam is communicated with said first radiation detector; and wherein said second x-ray beam passes through said patient so as to generate a second attenuated x-ray beam, wherein said second attenuated x-ray beam is communicated with said second radiation detector.

12. The method of claim 7, wherein said obtaining includes obtaining an imaging system having a patient support structure;

wherein said imaging system defines a patient cavity; and wherein said patient support structure is movingly associated with said imaging system so as to allow said patient support structure to be disposed within said patient cavity.

13. The method of claim 12, wherein said operating includes associating a patient with said patient support structure and disposing said patient support structure within said patient cavity.

14. The method of claim 12, wherein said operating includes operating said imaging system so as to cause said radiation source and said radiation detector apparatus to rotate around said patient cavity.

15. The method of claim 7, wherein said operating includes operating said imaging system so as to cause said radiation beam to pass through a patient.

16. The method of claim 7, wherein said processing includes super positioning said first detector data and said second detector data so as to create said image data.

17. The method of claim 7, wherein said processing includes processing said first detector data and said second detector data so as to differentiate between material characteristics, wherein said material characteristics include material type and material density.

18. The method of claim 7, wherein said processing includes processing said first detector data and said second detector data so as to implement a beam hardening correction scheme.

19. The method of claim 7, wherein said processing includes processing said first detector data and said second detector data so as to implement an imaging system correction scheme.

20. A medium encoded with a machine-readable computer program code for differentiating material characteristics using a hybrid scintillation/direct conversion imaging system, wherein the hybrid scintillation/direct conversion imaging system includes a radiation source and a radiation detector apparatus having a first radiation detector and a second radiation detector, said medium including instructions for causing controller to implement a method comprising:

operating the imaging system so as to cause said radiation source to emit a radiation beam toward said radiation detector apparatus such that said first radiation detector generates first detector data and said second radiation detector generates second detector data, wherein said first radiation detector is a scintillator/photo-sensor detector and wherein said second radiation detector is a direct conversion detector; and processing said first detector data and said second detector data so as to generate image data.

21. The medium of claim 20, wherein said operating includes associating a patient with a patient support structure and disposing said patient support structure within a patient cavity.

22. The medium of claim 20, wherein said operating includes operating said imaging system so as to cause said radiation source and said radiation detector apparatus to rotate around a patient cavity.

23. The medium of claim 20, wherein said operating includes operating said imaging system so as to cause said radiation beam to pass through a patient.

24. The medium of claim 20, wherein said operating includes operating said imaging system so as to cause a first x-ray emitter to project a first x-ray beam toward said first radiation detector and so as to cause a second x-ray emitter to project a second x-ray beam toward said second radiation detector;

wherein said first x-ray beam passes through a patient so as to generate a first attenuated x-ray beam, wherein said first attenuated x-ray beam is communicated with said first radiation detector; and wherein said second x-ray beam passes through said patient so as to generate a second attenuated x-ray beam, wherein said second attenuated x-ray beam is communicated with said second radiation detector.

25. The medium of claim 20, wherein said operating includes operating said imaging system so as to cause a first x-ray emitter to project a first x-ray beam toward said first radiation detector;

wherein said first x-ray beam passes through a patient so as to generate a first attenuated x-ray beam, wherein said first attenuated x-ray beam is communicated with said first radiation detector and said second radiation detector.

26. The medium of claim 20, wherein said processing includes super positioning said first detector data and said second detector data so as to create said image data.

27. The medium of claim 20, wherein said processing includes processing said first detector data and said second detector data so as to differentiate between material characteristics, wherein said material characteristics include material type and material density.

28. The medium of claim 20, wherein said processing includes processing said first detector data and said second detector data so as to implement a beam hardening correction scheme.

29. The medium of claim 20, wherein said processing includes processing said first detector data and said second detector data so as to implement an imaging system correction scheme.

30. A hybrid scintillation/direct conversion imaging system, comprising:

a gantry, wherein said gantry defines a patient cavity and includes a radiation source and a radiation detection apparatus, wherein said radiation detection apparatus includes a first radiation detector and a second radiation detector and wherein said radiation source and said radiation detection apparatus are rotatingly associated with said gantry in an X-Y plane so as to be separated by said patient cavity, wherein said first radiation detector is a different type of detector than said second radiation detector, said second radiation detector configured to count attenuated x-rays and measure the energy of said attenuated x-rays;

a patient support structure movingly associated with said gantry in a Z axis substantially transverse to said X-Y plane so as to allow communication with said patient cavity; and a processing device, for obtaining data from said first radiation detector and said second radiation detector.

31. The imaging system of claim 30, wherein said first radiation detector is a scintillator/photo-sensor detector and wherein said second radiation detector is a direct conversion detector.

32. The imaging system of claim 30, wherein said first radiation detector is disposed so as to be adjacent to said second radiation detector relative to said Z axis.

33. The imaging system of claim 30, wherein said first radiation detector is disposed so as to be non-adjacent to said second radiation detector relative to said Z axis and adjacent thereto with respect to said X-Y plane.

34. The imaging system of claim 30, wherein said radiation source includes a first radiation emitter opposingly disposed relative to said first radiation detector and wherein said radiation source includes a second radiation emitter opposingly disposed relative to said second radiation detector.

35. The imaging system of claim 30, wherein said radiation source includes a first radiation emitter opposingly disposed relative to said first radiation detector and said second radiation detector.

36. A method for differentiating material characteristics using a hybrid scintillation/direct conversion imaging system, wherein the hybrid scintillation/direct conversion imaging system includes a radiation source and a radiation detector apparatus having a first radiation detector and a second radiation detector, the method further comprising:

operating the imaging system so as to cause said radiation source to emit a radiation beam toward said detector apparatus such that said first radiation detector generates first detector data and said second radiation detector generates second detector data, wherein said first radiation detector is a scintillator/photo-sensor detector and wherein said second radiation detector is a direct conversion detector, and processing said first detector data and said second detector data so as to generate image data.

37. The data signal of claim 36, wherein said operating includes associating a patient with a patient support structure and disposing said patient support structure within a patient cavity.

38. The data signal of claim 36, wherein said operating includes operating said imaging system so as to cause said radiation source and said radiation detector apparatus to rotate around a patient cavity.

39. The data signal of claim 36, wherein said operating includes operating said imaging system so as to cause said radiation beam to pass through a patient.

40. The data signal of claim 36, wherein said operating includes operating said imaging system so as to cause a first x-ray emitter to project a first x-ray beam toward said first radiation detector and so as to cause a second x-ray emitter to project a second x-ray beam toward said second radiation detector;

wherein said first x-ray beam passes through a patient so as to generate a first attenuated x-ray beam, wherein said first attenuated x-ray beam is communicated with said first radiation detector; and wherein said second x-ray beam passes through said patient so as to generate a second attenuated x-ray beam, wherein said second attenuated x-ray beam is communicated with said second radiation detector.

41. The data signal of claim 36, wherein said operating includes operating said imaging system so as to cause a first x-ray emitter to project a first x-ray beam toward said first radiation detector;

wherein said first x-ray beam passes through a patient so as to generate a first attenuated x-ray beam, wherein said first attenuated x-ray beam is communicated with said first radiation detector and said second radiation detector.

42. The data signal of claim 36, wherein said processing includes super positioning said first detector data and said second detector data so as to create said image data.

43. The data signal of claim 36, wherein said processing includes processing said first detector data and said second detector data so as to differentiate between material characteristics, wherein said material characteristics include material type and material density.

44. The data signal of claim 36, wherein said processing includes processing said first detector data and said second detector data so as to implement a beam hardening correction scheme.

45. The data signal of claim 36, wherein said processing includes processing said first detector data and said second detector data so as to implement an imaging system correction scheme.

* * * * *